US010453324B2

(12) United States Patent
Minocha

(10) Patent No.: US 10,453,324 B2
(45) Date of Patent: Oct. 22, 2019

(54) TREADMILL SAFETY WARNING AND NOTIFICATION SYSTEM

(71) Applicant: Himanshu Minocha, Hopkinton, MA (US)

(72) Inventor: Himanshu Minocha, Hopkinton, MA (US)

(*) Notice: Subject to any disclaimer, the term of this patent is extended or adjusted under 35 U.S.C. 154(b) by 0 days.

(21) Appl. No.: 15/768,153

(22) PCT Filed: Oct. 14, 2016

(86) PCT No.: PCT/US2016/056984
§ 371 (c)(1),
(2) Date: Apr. 13, 2018

(87) PCT Pub. No.: WO2017/066527
PCT Pub. Date: Apr. 20, 2017

(65) Prior Publication Data
US 2018/0308334 A1    Oct. 25, 2018

Related U.S. Application Data

(60) Provisional application No. 62/400,166, filed on Sep. 27, 2016, provisional application No. 62/241,347, filed on Oct. 14, 2015.

(51) Int. Cl.
*G08B 21/04* (2006.01)
*A63B 22/02* (2006.01)
(Continued)

(52) U.S. Cl.
CPC ............ *G08B 21/043* (2013.01); *A61B 5/002* (2013.01); *A61B 5/0022* (2013.01); *A61B 5/1117* (2013.01); *A61B 5/6844* (2013.01); *A61B 5/6895* (2013.01); *A61B 5/746* (2013.01); *A63B 22/02* (2013.01); *A63B 24/0062* (2013.01); *G06Q 50/01* (2013.01); *G08B 21/0461* (2013.01); *G08B 25/001* (2013.01); *G08B 25/016* (2013.01); *G16H 40/67* (2018.01); *H04M 1/7253* (2013.01); *H04M 1/72533* (2013.01); *H04Q 9/00* (2013.01); *A61B 5/221* (2013.01); *A61B 2562/0219* (2013.01); *A61B 2562/0257* (2013.01); *A63B 22/0076* (2013.01); *A63B 22/04* (2013.01); *A63B 22/0605* (2013.01);
(Continued)

(58) Field of Classification Search
CPC .................... A63B 22/0242; A63B 2071/0625
USPC ..................................... 340/539.11
See application file for complete search history.

(56) References Cited

U.S. PATENT DOCUMENTS 5,314,391 A * 5/1994 Potash ............... A63B 22/0023
340/573.1
5,695,432 A   12/1997 Soderlund
(Continued)

OTHER PUBLICATIONS

International Search Report and Written Opinion for PCT/US2016/056984, dated Dec. 22, 2016.

*Primary Examiner* — Fabricio R Murillo Garcia
(74) *Attorney, Agent, or Firm* — Foley Hoag LLP

(57) ABSTRACT

Methods and systems are disclosed to detect whether a treadmill user is in the danger of falling off the treadmill and to accordingly warn the user via, e.g., audio and haptic feedback. In the event the runner falls off the treadmill and becomes hurt or unresponsive, the system can automatically notify emergency contacts, e.g., via phone calls or text messages.

10 Claims, 18 Drawing Sheets

(51) Int. Cl.

| | | |
|---|---|---|
| *A61B 5/00* | (2006.01) | |
| *A61B 5/11* | (2006.01) | |
| *G06Q 50/00* | (2012.01) | |
| *H04Q 9/00* | (2006.01) | |
| *G16H 40/67* | (2018.01) | |
| *A63B 24/00* | (2006.01) | |
| *G08B 25/00* | (2006.01) | |
| *G08B 25/01* | (2006.01) | |
| *H04M 1/725* | (2006.01) | |
| *A63B 71/06* | (2006.01) | |
| *A61B 5/22* | (2006.01) | |
| *A63B 22/00* | (2006.01) | |
| *A63B 22/04* | (2006.01) | |
| *A63B 22/06* | (2006.01) | |
| *H04W 4/90* | (2018.01) | |

(52) U.S. Cl.
CPC ....... *A63B 22/0664* (2013.01); *A63B 71/0622* (2013.01); *A63B 2024/0093* (2013.01); *A63B 2071/0625* (2013.01); *A63B 2071/0627* (2013.01); *A63B 2071/0655* (2013.01); *A63B 2207/02* (2013.01); *A63B 2220/10* (2013.01); *A63B 2220/13* (2013.01); *A63B 2220/20* (2013.01); *A63B 2220/802* (2013.01); *A63B 2220/805* (2013.01); *A63B 2220/89* (2013.01); *A63B 2225/20* (2013.01); *A63B 2225/50* (2013.01); *G08C 2201/93* (2013.01); *H04W 4/90* (2018.02)

(56) References Cited

U.S. PATENT DOCUMENTS

| | | | |
|---|---|---|---|
| 6,733,423 | B1 | 5/2004 | Chang |
| 7,862,476 | B2 | 1/2011 | Blau et al. |
| 2002/0045517 | A1 | 4/2002 | Oglesby et al. |
| 2010/0216599 | A1* | 8/2010 | Watterson .......... A63B 22/0242 482/4 |
| 2014/0135996 | A1 | 5/2014 | Yu |
| 2016/0023049 | A1* | 1/2016 | Dalebout .......... A63B 22/0242 482/7 |
| 2017/0203157 | A1* | 7/2017 | Volkerink ............... H04W 4/70 |
| 2017/0230734 | A1* | 8/2017 | Oleson ................. H04B 1/385 |

* cited by examiner

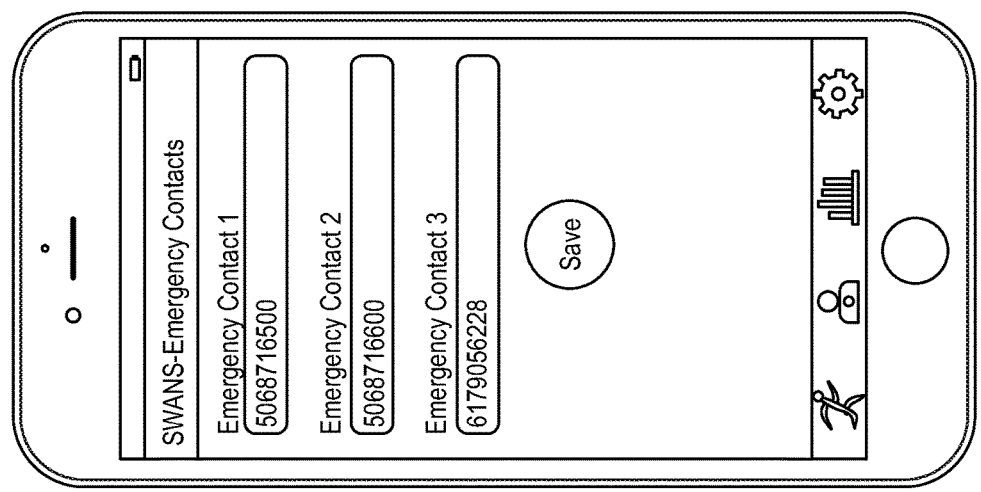
For iOS
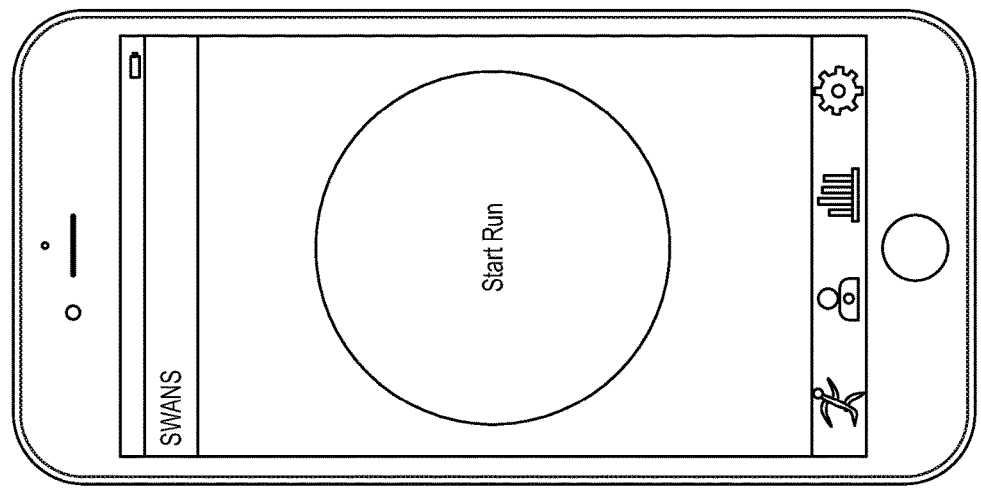
FIG. 10

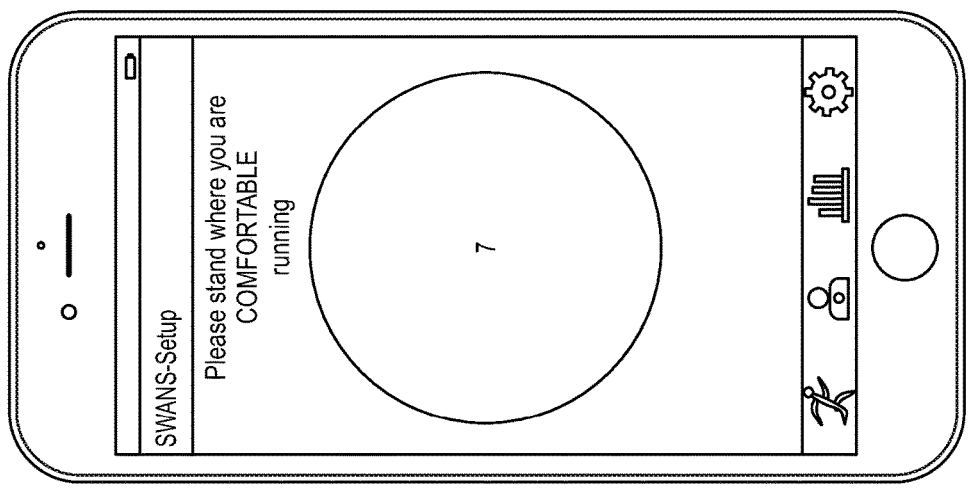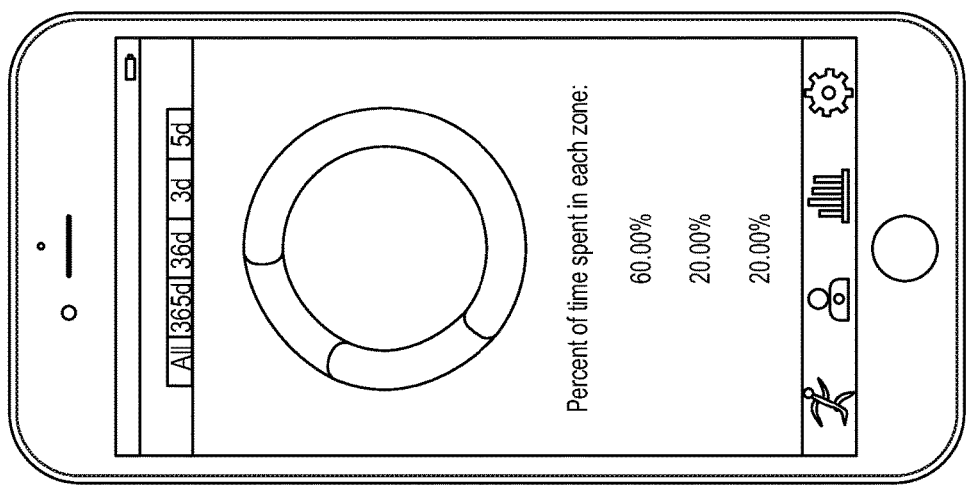
FIG. 10(cont.)

TESTING RESULTS

| Device | Action | Results | Test 1 | Test 2 | Test 3 | Test 4 | Test 5 | Test 6 |
|---|---|---|---|---|---|---|---|---|
| Apple IOS | Power on hardware | All components working with LED light on | Success | Success | Success | Success | Success | Success |
| Apple IOS | Install hardware on the treadmill dashboard | | Success | Success | Success | Success | Success | Success |
| Apple IOS | Runner in a stationary position on the treadmill | | | | | | | |
| Apple IOS | Launch SWANS App | Application launched Successfully | Success | Success | Success | Success | Success | Success |
| Apple IOS | Pair App with the Hardware | Successfully paired | Success | Success | Success | Success | Success | Success |
| Apple IOS | Runner to setup green zone | Green zone calibrated successfully | Success | Success | Success | Success | Success | Success |
| Apple IOS | Runner to setup yellow zone | Yellow zone calibrated successfully | Success | Success | Success | Success | Success | Success |
| Apple IOS | Runner to identify end of treadmill (Red zone) | Red zone calibrated successfully | Success | Success | Success | Success | Success | Success |
| Apple IOS | Set up emergency contacts | Emergency contact information saved successfully | Success | Success | Success | Success | Success | Success |
| Apple IOS | Main menu - tap "Start Run" | Application starts to collect data | Success | Success | Success | Success | Success | Success |
| Apple IOS | "Induce" Runner to move "with in" Green zone | No notifications sent | Success | Success | Success | Success | Success | Success |
| Apple IOS | "Induce" Runner to to move to Yellow zone | Haptic feedback on the mobile device | Success | Success | Success | Success | Success | Success |
| Apple IOS | "Induce" Runner to to stay in the Yellow zone | Audio feedback on the mobile device | Success | Success | Success | Success | Success | Success |
| Apple IOS | "Induce" Runner to step off the treadmill - simulating Red zone | Received "Are you ok" Notification | Success | Success | Success | Success | Success | Success |
| Apple IOS | Ask runner to press " I am OK" | No results expected | Success | Success | Success | Success | Success | Success |
| Apple IOS | Ask runner to start the App again and enter the green zone | No results expected | Success | Success | Success | Success | Success | Success |
| Apple IOS | "Induce" Runner to step off the treadmill - simulating Red zone | Received "Are you ok" Notification | Success | Success | Success | Success | Success | Success |
| Apple IOS | Ask runner to press " I need help" | Text message should be sent and phone call should go out automatically to the configured emergency contacts. Verify text/phone call received. | Success | Success | Success | Success | Success | Success |
| Apple IOS | Ask runner to start the App again and enter the green zone | No results expected | Success | Success | Success | Success | Success | Success |
| Apple IOS | "Induce" Runner to step off the treadmill - simulating Red zone | Received "Are you ok" Notification | Success | Success | Success | Success | Success | Success |
| Apple IOS | Ask runner to not respond - simulating a serious injury scenario | Text message should be sent and phone call should go out automatically to the configured emergency contacts. Verify text/phone call received. | Success | Success | Success | Success | Success | Success |

FIG. 14

| TESTING RESULTS | | | | | | | | |
|---|---|---|---|---|---|---|---|---|
| Device | Action | Results | Test 1 | Test 2 | Test 3 | Test 4 | Test 5 | Test 6 |
| Google/And | Power on hardware | All components working with LED light on | Success | Success | Success | Success | Success | Success |
| Google/And | Install hardware on the treadmill dashboard | | Success | Success | Success | Success | Success | Success |
| Google/And | Runner in a stationary position on the treadmill | | | | | | | |
| Google/And | Launch SWANS App | Application launched Successfully | Success | Success | Success | Success | Success | Success |
| Google/And | Pair App with the Hardware | Successfully paired | Success | Success | Success | Success | Success | Success |
| Google/And | Runner to setup green zone | Green zone calibrated successfully | Success | Success | Success | Success | Success | Success |
| Google/And | Runner to setup yellow zone | Yellow zone calibrated successfully | Success | Success | Success | Success | Success | Success |
| Google/And | Runner to identify end of treadmill (Red zone) | Red zone calibrated successfully | Success | Success | Success | Success | Success | Success |
| Google/And | Set up emergency contacts | Emergency contact information saved successfully | Success | Success | Success | Success | Success | Success |
| Google/And | Main menu - tap "Start Run" | Application starts to collect data | Success | Success | Success | Success | Success | Success |
| Google/And | "Induce" Runner to move "with in" Green zone | No notifications sent | Success | Success | Success | Success | Success | Success |
| Google/And | "Induce" Runner to to move to Yellow zone | Haptic feedback on the mobile device | Success | Success | Success | Success | Success | Success |
| Google/And | "Induce" Runner to to stay in the Yellow zone | Audio feedback on the mobile device | Success | Success | Success | Success | Success | Success |
| Google/And | "Induce" Runner to step off the treadmill - simulating Red zone | Received "Are you ok" Notification | Success | Success | Success | Success | Success | Success |
| Google/And | Ask runner to press " I am OK" | No results expected | Success | Success | Success | Success | Success | Success |
| Google/And | Ask runner to start the App again and enter the green zone | No results expected | Success | Success | Success | Success | Success | Success |
| Google/And | "Induce" Runner to step off the treadmill - simulating Red zone | Received "Are you ok" Notification | Success | Success | Success | Success | Success | Success |
| Google/And | Ask runner to press " I need help" | Text message should be sent and phone call should go out automatically to the configured emergency contacts. Verify text/phone call received. | | | | Success | Success | Success |
| Google/And | Ask runner to start the App again and enter the green zone | No results expected | Success | Success | Success | Success | Success | Success |
| Google/And | "Induce" Runner to step off the treadmill - simulating Red zone | Received "Are you ok" Notification | Success | Success | Success | Success | Success | Success |
| Google/And | Ask runner to not respond - simulating a serious injury scenario | Text message should be sent and phone call should go out automatically to the configured emergency contacts. Verify text/phone call received. | | | Success | Success | Success | Success |

FIG. 14(cont.)

| TESTING RESULTS | | | | | | | | |
|---|---|---|---|---|---|---|---|---|
| Device | Action | Results | Test 1 | Test 2 | Test 3 | Test 4 | Test 5 | Test 6 |
| WatchOS | Power on hardware | All components working with LED light on | Success | Success | Success | Success | Success | Success |
| WatchOS | Install hardware on the treadmill dashboard | | Success | Success | Success | Success | Success | Success |
| WatchOS | Runner in a stationary position on the treadmill | | | | | | | |
| WatchOS | Launch SWANS App | Application launched Successfully | Success | Success | Success | Success | Success | Success |
| WatchOS | Pair App with the Hardware | Successfully paired | Success | Success | Success | Success | Success | Success |
| WatchOS | Runner to setup green zone | Green zone calibrated successfully | Success | Success | Success | Success | Success | Success |
| WatchOS | Runner to setup yellow zone | Yellow zone calibrated successfully | Success | Success | Success | Success | Success | Success |
| WatchOS | Runner to identify end of treadmill (Red zone) | Red zone calibrated successfully | Success | Success | Success | Success | Success | Success |
| WatchOS | Set up emergency contacts | Emergency contact information saved successfully | Success | Success | Success | Success | Success | Success |
| WatchOS | Main menu - tap "Start Run" | Application starts to collect data | Success | Success | Success | Success | Success | Success |
| WatchOS | "Induce" Runner to move "with in" Green zone | No notifications sent | Success | Success | Success | Success | Success | Success |
| WatchOS | "Induce" Runner to to move to Yellow zone | Haptic feedback on the mobile device | Success | Success | Success | Success | Success | Success |
| WatchOS | "Induce" Runner to to stay in the Yellow zone | Audio feedback on the mobile device | Success | Success | Success | Success | Success | Success |
| WatchOS | "Induce" Runner to step off the treadmill - simulating Red zone | Received "Are you ok" Notification | Success | Success | Success | Success | Success | Success |
| WatchOS | Ask runner to press "I am OK" | No results expected | Success | Success | Success | Success | Success | Success |
| WatchOS | Ask runner to start the App again and enter the green zone | No results expected | Success | Success | Success | Success | Success | Success |
| WatchOS | "Induce" Runner to step off the treadmill - simulating Red zone | Received "Are you ok" Notification | Success | Success | Success | Success | Success | Success |
| WatchOS | Ask runner to press "I need help" | Text message should be sent and phone call should go out automatically to the configured emergency contacts. Verify text/phone call received. | Success | Success | Success | Success | Success | Success |
| WatchOS | Ask runner to start the App again and enter the green zone | No results expected | Success | Success | Success | Success | Success | Success |
| WatchOS | "Induce" Runner to step off the treadmill - simulating Red zone | Received "Are you ok" Notification | Success | Success | Success | Success | Success | Success |

FIG. 14(cont.)

TESTING RESULTS

| Device | Action | Results | Test 1 | Test 2 | Test 3 | Test 4 | Test 5 | Test 6 |
|---|---|---|---|---|---|---|---|---|
| WatchOS | Ask Runner to not respond-simultating a serious injury scenari | Text message should be sent and phone call should go out automatically to the configured emergency contacts. verify text/ phone calls received. | Success | Success | Success | Success | Success | Success |
| Apple TVOS | Power on hardware | All components working with LED light on | Success | Success | Success | Success | Success | Success |
| Apple TVOS | Install hardware on the treadmill dashboard | | Success | Success | Success | Success | Success | Success |
| Apple TVOS | Runner in a stationary position on the treadmill | | | | | | | |
| Apple TVOS | Launch SWANS App | Application launched Successfully | Success | Success | Success | Success | Success | Success |
| Apple TVOS | Pair App with the Hardware | Successfully paired | Success | Success | Success | Success | Success | Success |
| Apple TVOS | Runner to setup green zone | Green zone calibrated successfully | Success | Success | Success | Success | Success | Success |
| Apple TVOS | Runner to setup yellow zone | Yellow zone calibrated successfully | Success | Success | Success | Success | Success | Success |
| Apple TVOS | Runner to identify end of treadmill (Red zone) | Red zone calibrated successfully | Success | Success | Success | Success | Success | Success |
| Apple TVOS | Set up emergency contacts | Emergency contact information saved successfully | Success | Success | Success | Success | Success | Success |
| Apple TVOS | Main menu - tap "Start Run" | Application starts to collect data | Success | Success | Success | Success | Success | Success |
| Apple TVOS | "Induce" Runner to move "with in" Green zone | No notifications sent | Success | Success | Success | Success | Success | Success |
| Apple TVOS | "Induce" Runner to to move to Yellow zone | Haptic feedback on the mobile device | Success | Success | Success | Success | Success | Success |
| Apple TVOS | "Induce" Runner to to stay in the Yellow zone | Audio feedback on the mobile device | Success | Success | Success | Success | Success | Success |
| Apple TVOS | "Induce" Runner to step off the treadmill - simulating Red zone | Received "Are you ok" Notification | Success | Success | Success | Success | Success | Success |
| Apple TVOS | Ask runner to press "I am OK" | No results expected | Success | Success | Success | Success | Success | Success |
| Apple TVOS | Ask runner to start the App again and enter the green zone | No results expected | Success | Success | Success | Success | Success | Success |

FIG. 14(cont.)

TREADMILL SAFETY WARNING AND NOTIFICATION SYSTEM

CROSS-REFERENCE TO RELATED APPLICATIONS

This application is the U.S. national phase of International Patent Application No. PCT/US16/056984 filed on Oct. 14, 2016 entitled TREADMILL SAFETY WARNING AND NOTIFICATION SYSTEM, which claims the benefit of U.S. Provisional Application No. 62/400,166, filed on 27 Sep. 2016, and U.S. Provisional Application No. 62/241,347, filed on 14 Oct. 2015; the entire contents of each of said applications are incorporated herein in their entirety by this reference.

BACKGROUND OF THE INVENTION

The Consumer Product Safety Commission reported in 2014 that there were 24,000 emergency room cases related to treadmills (Fottrell, *MarketWatch*, May 5, 2015. Web. Accessed Jun. 12, 2016). Moreover, there were an average of three deaths per year related to such incidents between 2003 and 2012. In a high profile example, David Goldberg, the former CEO of Survey Monkey, fell off a treadmill on May 1, 2015 and thereby died of head trauma and bleeding (Goel and Randal, *The New York Times*. The New York Times, May 4, 2015; Web. Accessed Jun. 12, 2016; *Washington Post*. The Washington Post, n.d. Web. Jun. 12, 2016). Mr. Goldberg went to run at around 4 P.M. in the afternoon and was discovered by his brother at 7 P.M. in a state of unconsciousness albeit alive. Nobody was notified when Mr. Goldberg fell and during a time period when health interventions could have been performed to increase the likelihood of survival.

These facts highlight that treadmills are the most dangerous type of exercise equipment that people use. Treadmills are so popular that over 50 million people use them every year and they continually outsell all other types of exercise equipment by a large margin. In addition, the number of treadmill related injuries has nearly tripled in the past 20 years due to the fact that running is becoming increasingly popular and that many people, especially in colder climates, choose to run on a treadmill for exercise purposes. Also, accidents are on the rise because people are becoming more distracted when they run by, for example, TVs, books, and other portable personal electronic entertainment devices. In the three years following the introduction of the iPhone®, the number of treadmill-related accidents rose more than 45% (see Injury Statistics. *U.S. Consumer Product Safety Commission*. Web. Jun. 12, 2016).

There are devices that have tried to prevent these injuries. The most common solution is the use of a safety key. There are little to no statistics related to this device, but based on anecdotal evidence, very few people use this device. Many people find the safety key intrusive. In addition, safety keys are not user-configurable and provide no means of notification to other people (e.g., emergency contacts) for help. Another popular approach is the harness and suspension system (as exemplified, for example, in U.S. Pat. No. 5,695,432, or as shown in Kaye® Suspension Walkers, Kaye Products, Inc., Hillsborough, N.C.). This type of system has many drawbacks, including extreme monetary expense and invasiveness that is more than that for safety keys. Harness and suspension treadmills are also pre-configured such that they do not work on all treadmills and/or do not generally conform for useability for everyone. If a runner falls and injures herself, there is no mechanism in place that would notify anybody else, such as emergency contacts. Other similar exercise or entertainment devices (such as those disclosed in U.S. Pat. No. 7,862,476, or Reharunner treadmills shown on the web site of Chinesport) generally have the same problems.

No seamless systems is available on the market that prevent, warn if a runner is about to fall, or notify emergency contacts in the even that a runner falls. Accordingly, there is a great need in the art for more improved safety devices.

BRIEF DESCRIPTION OF THE DRAWINGS

FIG. 10 depicts different interfaces of the SWANS software on Apple iPhone systems (iOS).

FIG. 14 depicts various positive test results for different functions on different Operation Systems (OSs) for SWANS.

DETAILED DESCRIPTION

Figure 1:
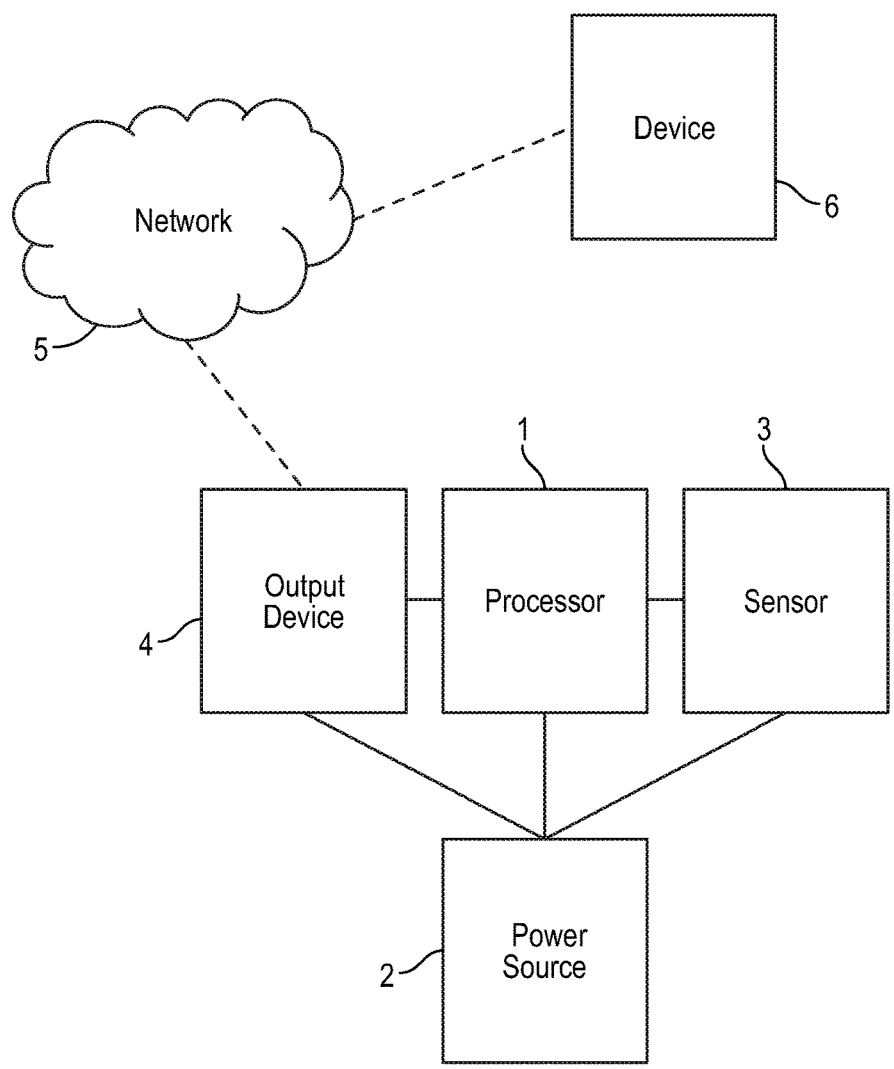
FIG. 1 schematically shows a device for providing distance feedback on a treadmill, detecting an accident, and sending a notification.

FIG. 1 schematically shows one embodiment of a device for providing distance feedback on a treadmill, detecting an accident, and sending a notification. A processor 1 is operably connected to a power source 2, for example, a battery or electrical outlet. The processor 1 and battery 2 are also connected to a sensor 3. The sensor 3 is capable of detecting a position of a user of the treadmill. The sensor 3 can be, for example, an ultrasonic sensor, an optical sensor, radar sensor, an infra-red sensor, or a capacitive sensor. The sensor can either actively interrogate the distance to the user, for example by emitting an ultrasonic or electromagnetic pulse and detecting the reflection, or by passively detecting the position of the user, for example by capacitive sensing. The sensor can measure the distance to the user at a predetermined frequency, for example 100, 300, 500, 1000, 2000, or 3000 times per second.

The processor 1 is also connected to an output device 4. The output device 4 can, for example, provide a visual, audio and/or haptic output to a user or another person or persons. For example, the output 4 can employ a flashing light, an alarm sound, and/or a vibration. The output device 4 can also, or alternatively, provide a signal, either wired or wireless. The signal can be transmitted to another device, for example by Bluetooth™, or to a network 5. The network can be, for example, the Internet, or a wired or wireless local area network. The network 5 can in turn relay the signal to another device 6, for example a computer, tablet, phone, smartphone, watch, smartwatch, pager, or other networked device or wearable technology. The signal can be configured to be received at the device 6 as, for example, an email, a text message, a posting on a social media system, or the like.

The processor 1 is configured to receive signals from the sensor 3, the signals being indicative of the position of a person relative to the treadmill. The processor 1 is programmed to interpret the signals from the sensor 3 in order to determine whether the person is in a desired position relative to the treadmill, for example, whether the person is in a "safe" position correctly positioned on the treadmill, or off the end of the treadmill, or somewhere in between. The user can input their desired parameters so that the processor 1 will correctly interpret the distances measured by the sensor 2. For example, users' size can vary leading to different distances falling within the tolerances of the "safe" position. Also, different treadmills can be sized differently.

The processor 1 can be programmed to activate the output device 4 to output a signal indicative of the state the person relative to the treadmill. For example, the processor 1 can be programmed to cause the output device 4 to visually display a green signal when the person is correctly positioned on the treadmill, a yellow signal when the person is on the treadmill but incorrectly positioned, and a red signal when the person is off the treadmill. The processor 1 can be programmed to provide haptic feedback, such as a vibration in the output device or a treadmill handle, when the user goes from correctly positioned on the treadmill to incorrectly positioned on the treadmill. Similarly, the processor 1 could be programmed to cause the output device to sound an audible alarm when the user goes from correctly positioned on the treadmill to incorrectly positioned on the treadmill, or when a user exits the treadmill.

The processor 1 can also be programmed to provide an alert to an external device when the position of the user changes from correctly positioned on the treadmill to incorrectly positioned on the treadmill, or when a user exits the treadmill. The processor 1 can transmit a signal directly, for example via a wired connection or a wireless connection such as a Bluetooth™ connection, to a device such as a phone, smartphone, watch, smartwatch, pager, tablet, computer or wearable technology, the signal indicating that the position of the user has changed. Similarly, the processor 1 can transmit such a signal to such a device via a network such as the internet or a LAN. The signal can result in, for example, an email, a text message, haptic feedback, such as a vibrating alert, and the like. The signal and/or resulting output therefrom can be transmitted to one or more recipients, such as one or more computers, electronic devices, persons, call centers, and the like. The processor 1 can transmit such a signal immediately, or the signal can be delayed by a predetermined amount of time. If the signal is delayed, the user can be able to prevent the signal from being sent, for example, if the user exited the treadmill intentionally, and there is no need to send an alert signifying a potentially dangerous situation. The predetermined time of delay can be adjustable by the user, and can be, for example, 5, 10, 15, 20, 30, 45, 60 or 90 seconds.

The system is configured to be modular, portable, and easily attachable to the dashboard of a treadmill. In one embodiment, the system is configured as or within a mobile consumer electronic device, such as an Apple iPhone device, Google Android device, Microsoft Windows™ device, and the like. Because the device is portable, it can be configured to clip or otherwise attached to a wide variety of treadmills and similar devices, such as elliptical machines, stationary bicycles, stair climbing machines, rowing machines, and the like, using a suitable mount such that no modification (e.g., internal or external) to the treadmill or similar device is required. The mount can simply provide a location for the device to be in a position in such a manner that the distance to the user is consistently measureable. The device can also be attached to or otherwise integrated into any other apparatus in which the position of a user can change over time, and an alert to such change is desirable.

One method related to devices like the one described above is as follows: Attach the device in a fixed position relative to the expected position of the user. Position the user at a distance or distances from the indicative of correct positioning, incorrect positioning, and exit, and cause the processor to record those distances and measured by the sensor. If necessary, provide the processor with additional pre-set inputs, such as desired methods of alert in case of a detected exit, device or devices or network addresses to which such alerts should be sent, volume of audible alerts, brightness and/or color of visual alerts, time-delay in sending alerts, etc. Begin an active monitoring mode in which the device will alert to sufficient movement of the user. If an alert is activated, either abort the alert, or allow it to be transmitted.

Figure 2A:
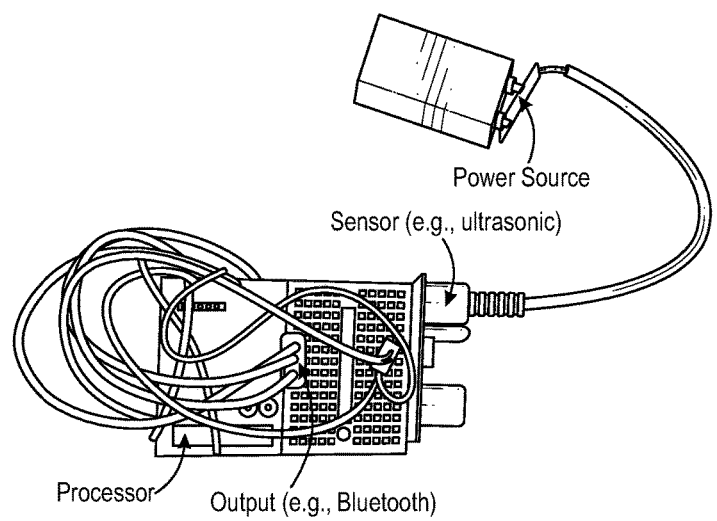
FIG. 2 shows a representative embodiment of a device of the present invention.
Figure 2B:
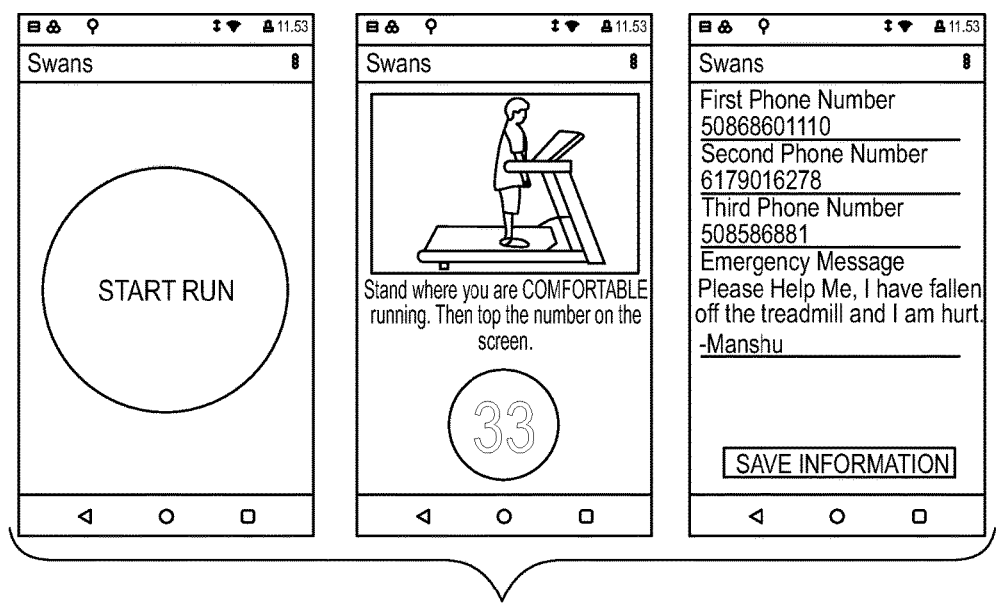

FIG. 2 provides a representative embodiment of a device of the present invention in which the device along with representative images of a user interface are shown. Representative sensors and outputs (e.g., ultrasonic and Bluetooth™) provide the position of a user over time based upon the distance detected between a user and the device and the ability to remotely notify one or more contacts. The representative device also allows for input of desired and/or undesired distances between the user and the device. The user can also input remote contact information and one or more messages to remotely notify contacts in the event that the user reaches an undesired distance from the device. The remote notification contact can be sent automatically immediately or after a predetermined amount of time. Alternatively, the output can be canceled based on local or remote instructions to override the remote notification, such as can occur if the user has voluntarily ended an exercise session and safely exceeds the set undesired distance by exiting the exercise environment prior to switching off the device.

EXAMPLES

The invention now being generally described, it will be more readily understood by reference to the following examples, which are included merely for purposes of illustration of certain embodiments and embodiments of the present invention, and are not intended to limit the invention.

Example 1

A system can include a processor, a sensor, an output device and a power source. The processor, the sensor and the output device can be operatively connected to the power source. The sensor can be configured to sense the distance from the sensor to a user. The processor can be configured to receive a signal from the sensor indicative of the distance from the sensor to the user. The processor can be configured to determine whether the distance is within a predetermined safe range. The processor can be configured to activate the output device based on the determination of whether the distance is within the predetermined safe range.

Some such systems can also include a mount that is fixedly attached to some or all of the processor, the sensor, the output device and the power source. The mount can be configured to attach the system to an apparatus, the user's position relative to the apparatus being variable. The apparatus can be, for example, a treadmill.

In some such systems, the sensor can be or include (a) an ultrasonic sensor, (b) an infrared sensor, (c) an optical sensor, (d) a radar sensor, or (e) a capacitive sensor. In some such systems the output device can be configured to provide an output as one or more of (a) a visual output, (b) an audio output, (c) a haptic output or (d) an electronic message output. The output is a message that is output can be a computer network. The output can be one or more of a text, an email, a phone call, or an alert on a social network, and/or provide the output to the user, such as via a wearable device. The output can be directed to a device associated with a person other than the user. The computer network can include or be one or more of (a) the internet and (b) a local area network.

In some such systems, the processor can be configured to determine whether the distance from the sensor to the user is within a predetermined warning range that is disjoint from the safety range, and the processor can also be configured to activate the output device based on the determination of whether the distance from the sensor to the user is within (a) the predetermined safe range, (b) the predetermined warning range, or (c) neither. In some such systems, activation of the output device can be overridden by the user.

Example 2

Additional exemplary systems are provided herein. Smart Safety Warning & Notification System For Treadmills (SWANS) is a seamless solution to warn a treadmill user (via, e.g., audio and haptic feedback), if the user is perceived to be in the danger of falling off the treadmill. In the event that a runner falls off the treadmill and become critically hurt or unresponsive, the system will automatically notify emergency contacts via phone calls and text messages including the runners GEO location so that they can get the help they need.

Figure 3:
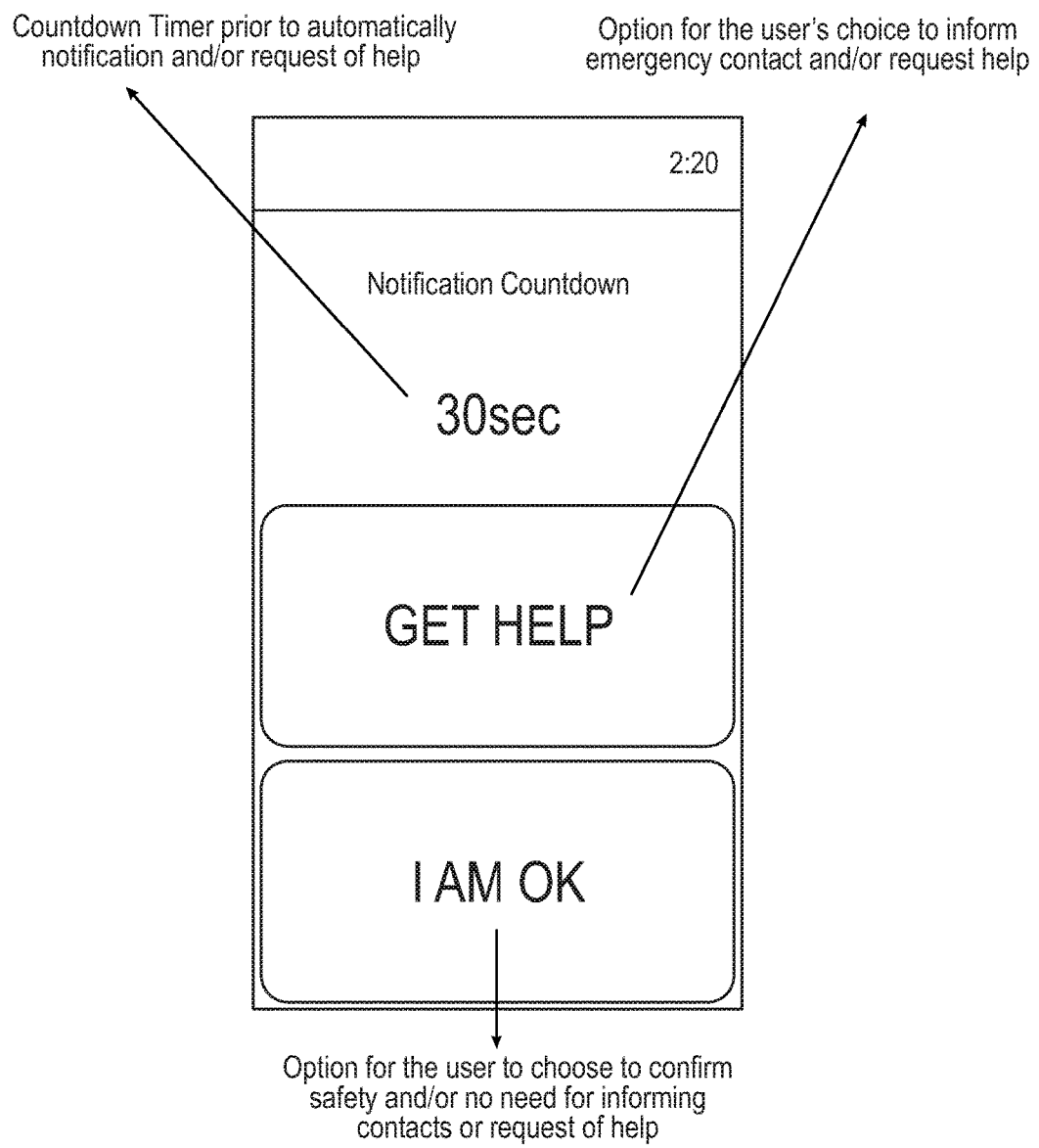
FIG. 3 depicts an exemplary notification interface showing the emergency notification prompt for the user's action.

This can be accomplished, in one embodiment, by splitting the treadmill into several zones, such as 2, 3, 4, 5, 6, or more zones, e.g., three virtual zones. For example, the Green Zone is where the runner is in their comfort zone, so there will be no feedback given to the user. Such comfort zone can be pre-defined and later changeable by the manufacturer of the treadmill, the operator and/or the maintenance service for the treadmill (e.g., a gym), or by the user herself. The Yellow Zone is when the distance from the user is out of the comfort zone. They will then get, e.g., sound and/or haptic feedback from a device wearable to the arm or the body of the user, signifying they are outside the comfort zone, so that they can attempt to get back into their comfort zone again. The Red zone happens when the user has crossed the Yellow zone boundary and is most likely to fall off the treadmill. The user can then get a notification, containing, e.g., two options. The first option is to dismiss the notification by which the user confirms her safety or capacity of avoiding any major injuries. The second option is to notify, e.g., three pre-defined emergency contacts, in the situation that the user is hurt or concerned about her health status. If there is no response to the notification within, e.g., 30 seconds, at least one, or any number of the runner's pre-set emergency contacts, is notified, e.g., through a text, an email, a phone call, or an alert on a social network, etc. An exemplary notification interface (either on the screen of the system, of the treadmill display, or an electronic device (e.g., a smartphone the user holds or in her arm's reach) is shown in FIG. 3.

Figure 4:
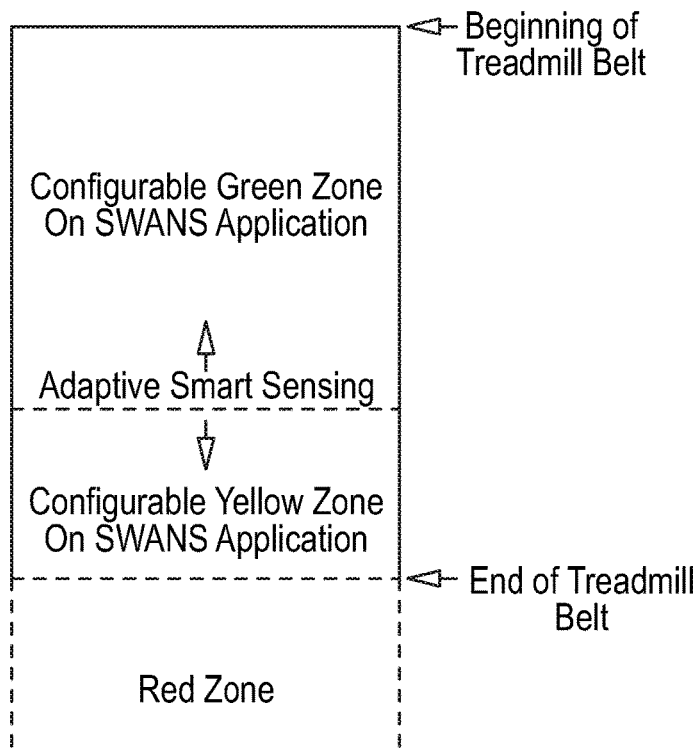
FIG. 4 depicts a virtual partitioning of the treadmill belt into Green, Yellow, and Red zones. In this embodiment, the partition of the Green and Yellow zone is adjustable to customize customer or the user needs.

These zones can, for example, be user-configured using a piece of hardware mounted on the treadmill dashboard. This hardware calculates how far the runner is from the dashboard and transmits the data via, e.g., Bluetooth™ technology (e.g., Bluetooth™ 4.0). The data are received on a mobile device and using three simple taps the zones can be configured. The previously mentioned zones can be pre-defined or defined the first time the user steps on the treadmill, through the setting in the system, in the treadmill display, or in an electric device (e.g., an application in a mobile phone). The mobile app that is used to set up these different zones allows the runner to choose where they are most comfortable running. If they like to run close to the dashboard they could have a small Green Zone and a large Yellow Zone, but if a runner likes running away from the dashboard they could have a large Green Zone and a small Yellow Zone. The Red zone can be set in the same way, or, more preferably, pre-set by the manufacturer, the operator, or the maintenance service for the treadmill but not editable by the user. The Red zone is always the end of the treadmill where a user can fall from. The partitioning of the belt is illustrated in FIG. 4.

Each zone invokes a different response from the device. For example, no feedback or a feedback showing safety can be provided to the user in the Green Zone. When the user enters the Yellow zone, haptic, audio, and/or visual feedback can be sent to the user for warning and action. If the runner falls or needs help or is unresponsive for warning, phone calls, text messages, emails, or other contacts, optionally with geographic location of the user, can be sent to pre-set emergency contacts.

Figure 5:
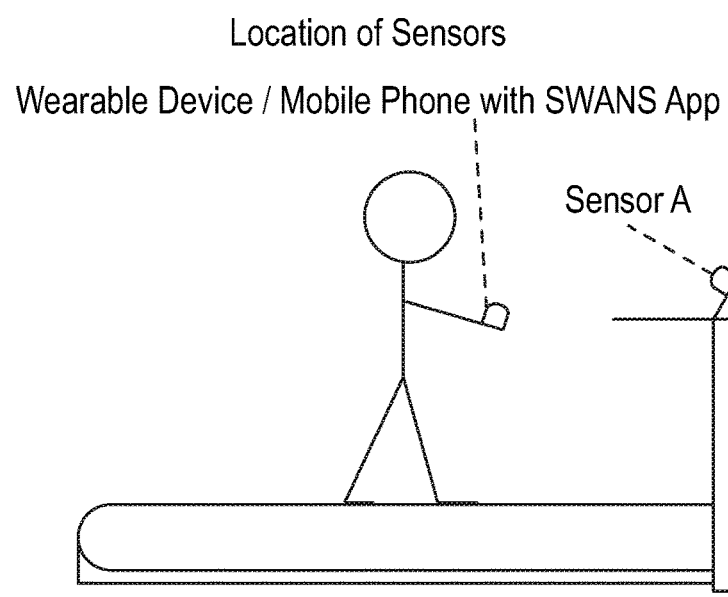
FIG. 5 depicts the position of two exemplary sensors (Sensor A on the treadmill and Sensor B or a wearable device (e.g., mobile phones with SWANS App).

In some embodiments, SWANS uses two sensors to check which zone within which the user is running. Each sensor is located in a different place. For example, a Bluetooth™-enabled sensor can be placed proximal to the treadmill, such as under the dashboard of the treadmill (Sensor A). This sensor contacts the second sensor such as a Wearable Device for, e.g., 1000 times a second, in order to quickly and accurately get distance information. To remove the margin of error caused by the treadmill moving, a gyroscope is used to compensate the inaccuracy in the distance. In any embodiment of the present invention described herein, an accelerometer can be used instead of or in addition to a gyroscope. The second sensor (Wearable Device) is a wearable device (a device for a user to wear on any part of the body (e.g., arm, trunk, head, etc.) or on the clothes, hat, glasses, necklace, or other accessories) that can give haptic and/or sound feedback to the user. This wearable device can contain Bluetooth™ technology and be able to send and receive notifications with the same Bluetooth™ technology or other technology known in the art. One exemplary position scheme for a two sensor system is shown in FIG. 5.

Figure 6:
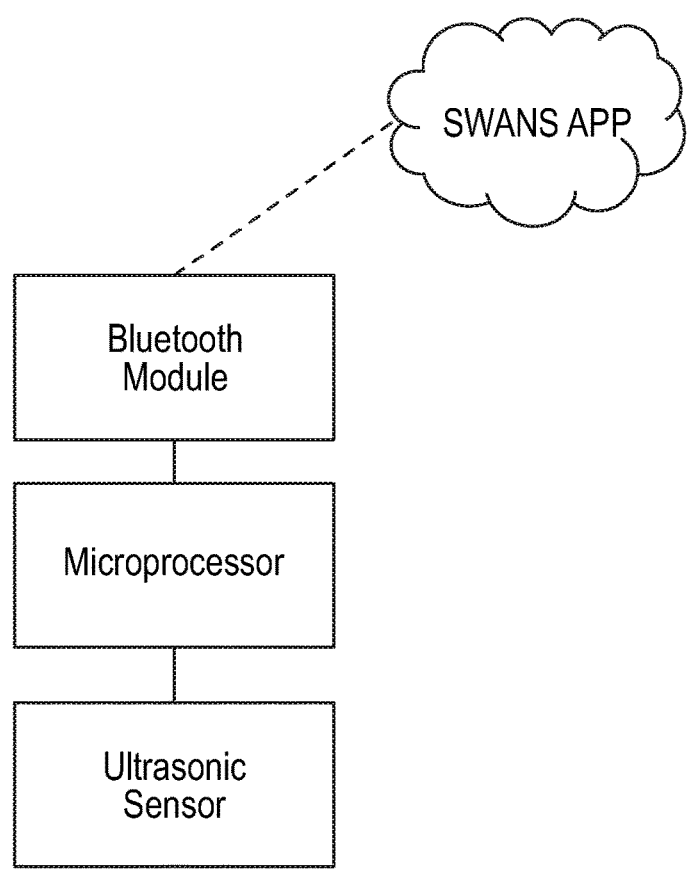
FIG. 6 depicts an exemplary hardware architecture.

In some embodiments, the hardware architecture of an exemplary SWANS system consisted of a Microprocessor, Bluetooth™ Module and an Ultrasonic Sensor (FIG. 6). The ultrasonic sensor gets the runners distance from the dashboard and this data is then routed through the microprocessor to the Bluetooth™ 4.0 Module. This Module can transmit the data in the form of a Byte array of length 2 to the mobile.

Figure 7:
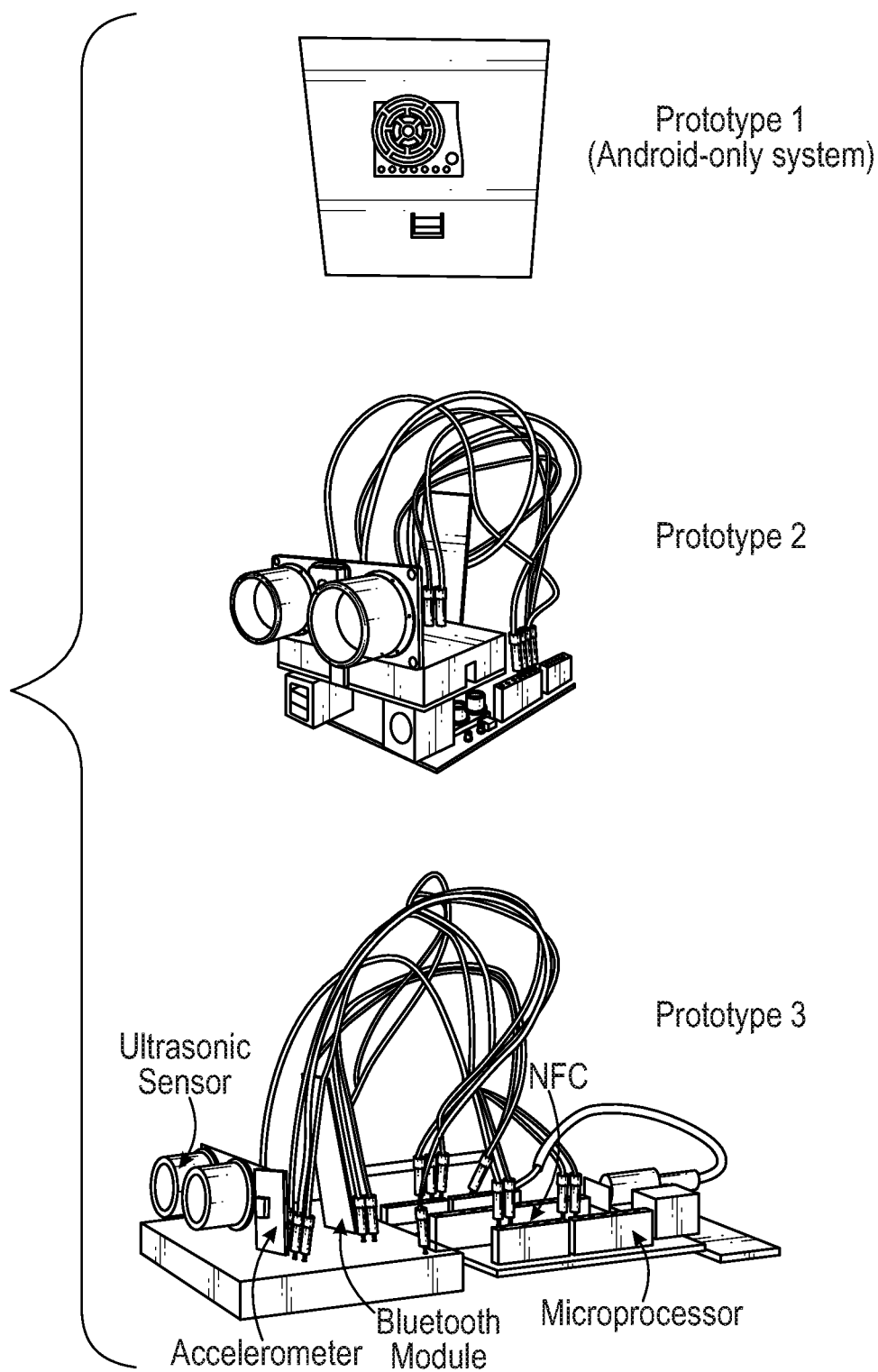
FIG. 7 depicts three exemplary prototypes of Sensor A of the SWANS system.
Figure 8:
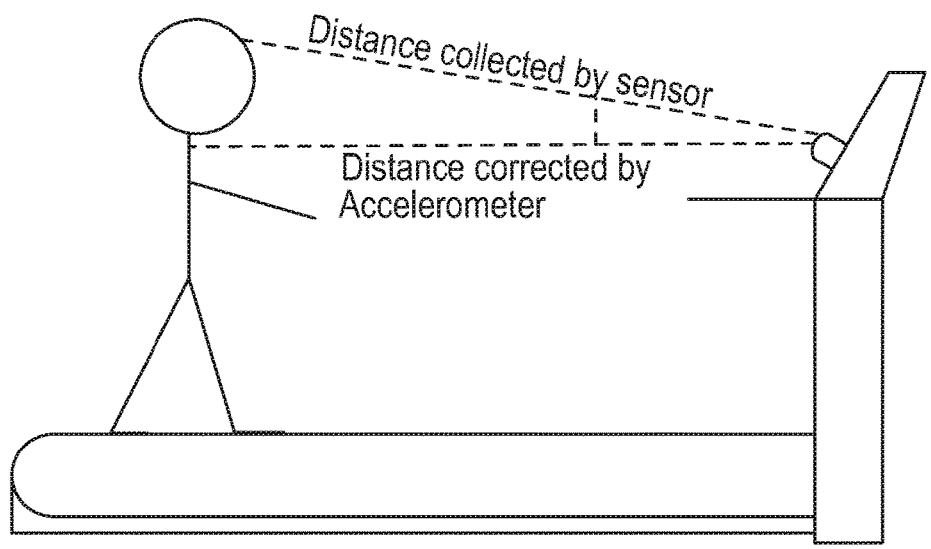
FIG. 8 depicts the mechanism for a gyroscope to correct distance readings.

Different embodiments of the SWANS system are also contemplated, as shown in FIG. 7. For example, the Prototype 2 contains iOS capabilities, and the ultrasonic sensor was changed to an SR-04 Ultrasonic Rangefinder. WatchOS was also added as a platform for SWANS. Prototype 3 added TVOS, Near-field communication (NFC), and Gyroscope capabilities. NFC enables easy pairing with Android phones. This was done using the "Tap to Pair" mechanism. A gyroscope or hardware or software having the function of a gyroscope is used for stabilization in the event that the treadmill's incline is changed, or when the treadmill is shaking or unsteady due to the user's running. The mechanism for stabilization can be seen in FIG. 8

Figure 9:
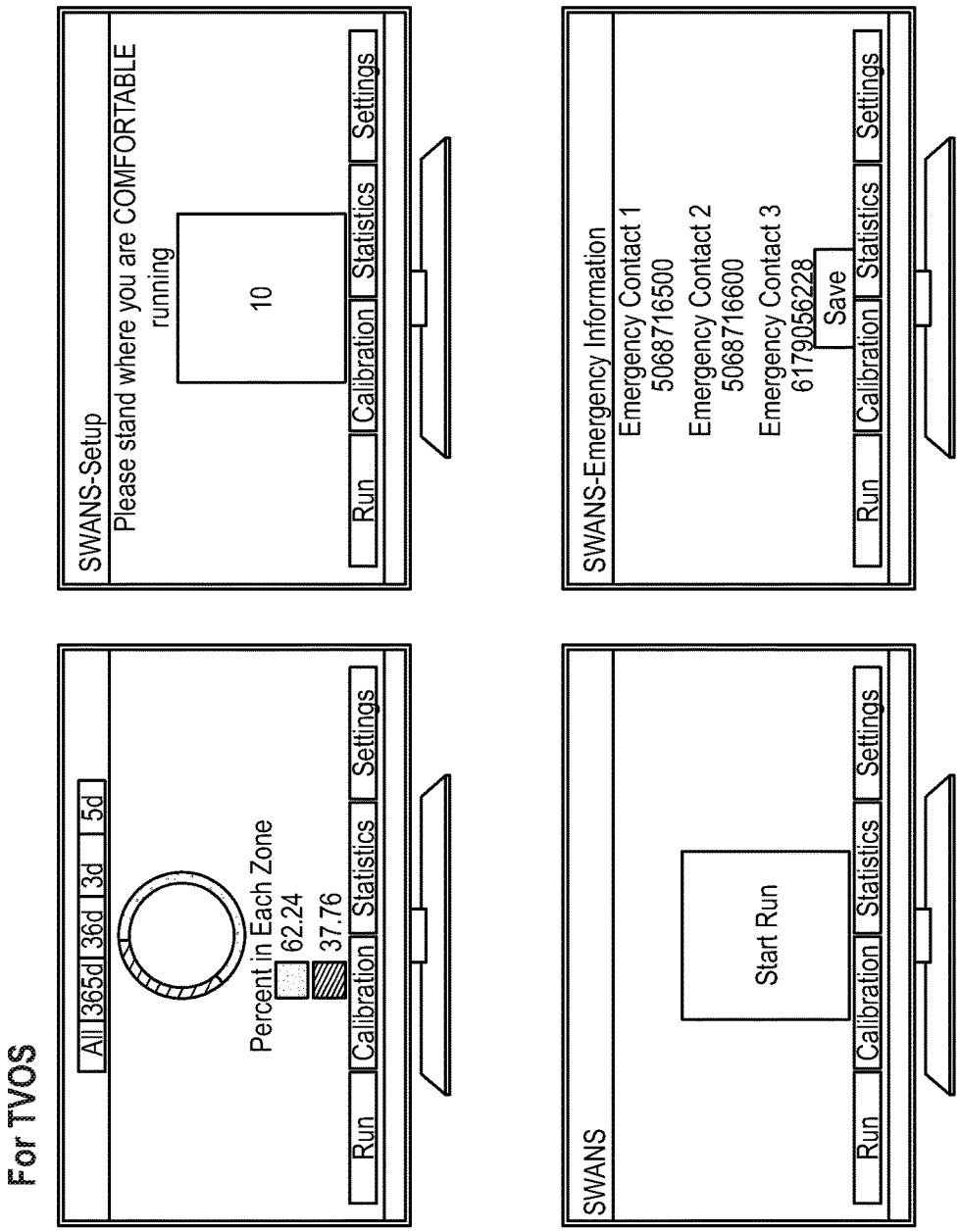
FIG. 9 depicts different interfaces of the SWANS software on TV systems (TVOS), such as status display, calibration, start action or status display, and the emergency contact list.
Figure 11:
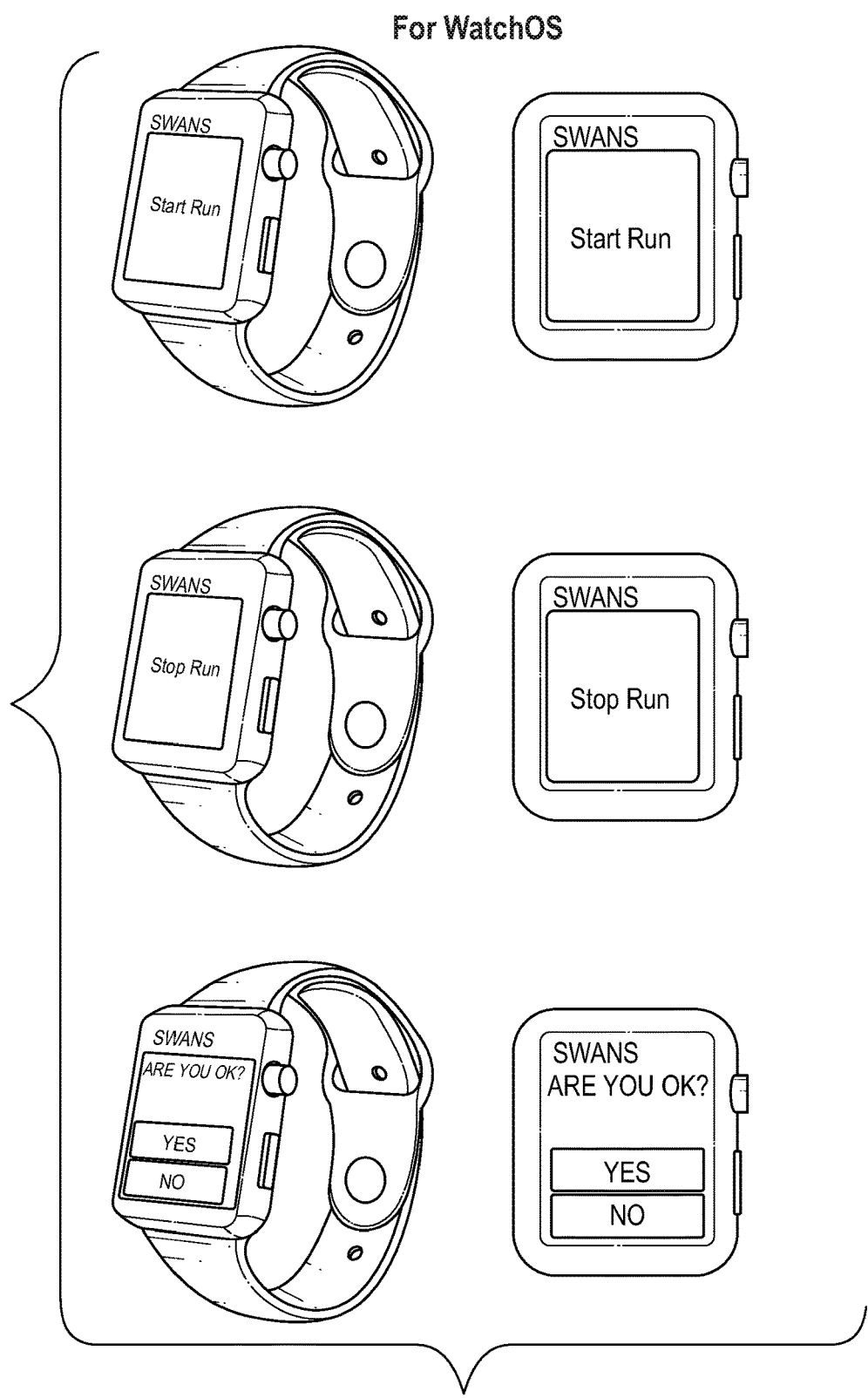
FIG. 11 depicts different interfaces of the SWANS software on watch systems (WatchOS).

Exemplary diagrams of computer program or application interfaces associated with SWANS are seen in FIGS. 9-11.

The SWANS system can use a computer program or application (e.g., on the wearable device) for user's display, notification, and control (e.g., of sending out emergency information and/or request of help). An exemplary application can have multiple interfaces. The first interface contains a Calibration screen, displaying set up instructions and a single button. The user uses this interface to configure parameters for her using the treadmill (e.g., the end place of the treadmill, etc.). This interface can provide all the information the user needs to get the various feedback mechanisms built into the software. The second interface is an Emergency contacts screen. On this screen a user can indicate who their three or more predefined emergency contacts are. A user can further choose if they want auto calibrating zones and the amount of time wanted before the emergency contacts are notified that a runner has fallen. The third interface is a Start/Stop run screen. On this screen a user can start or stop a run either initiating the respective feedback mechanisms or disabling them. The final interface is a statistics page. The data on this page are used to adjust the green and yellow zones in order to prevent unnecessary haptic feedback and audio feedback.

Figure 12:
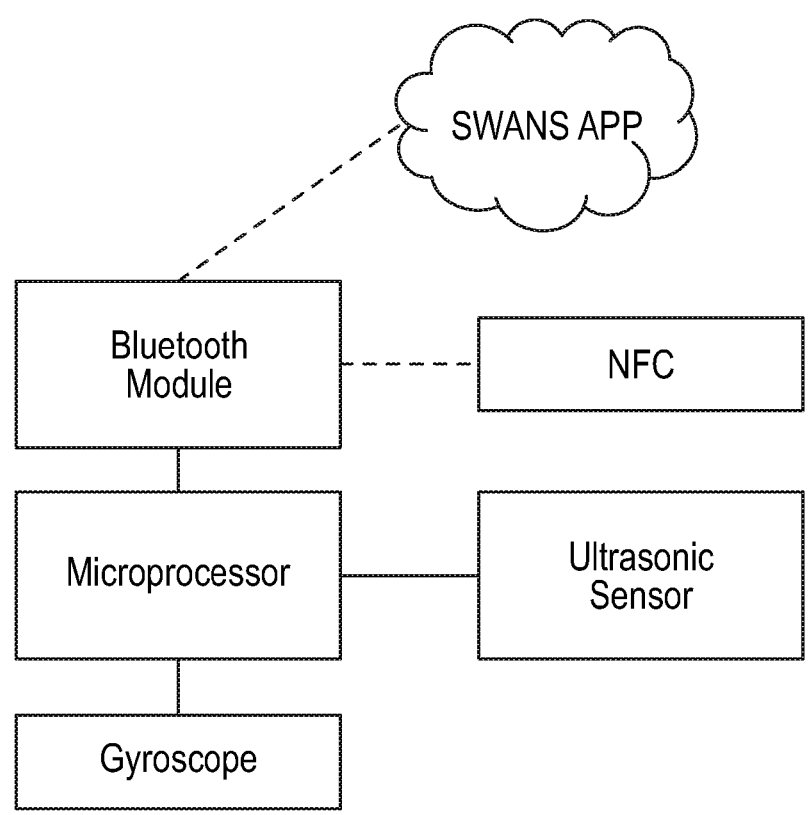
FIG. 12 depicts an exemplary final hardware architecture for SWANS.
Figure 13:
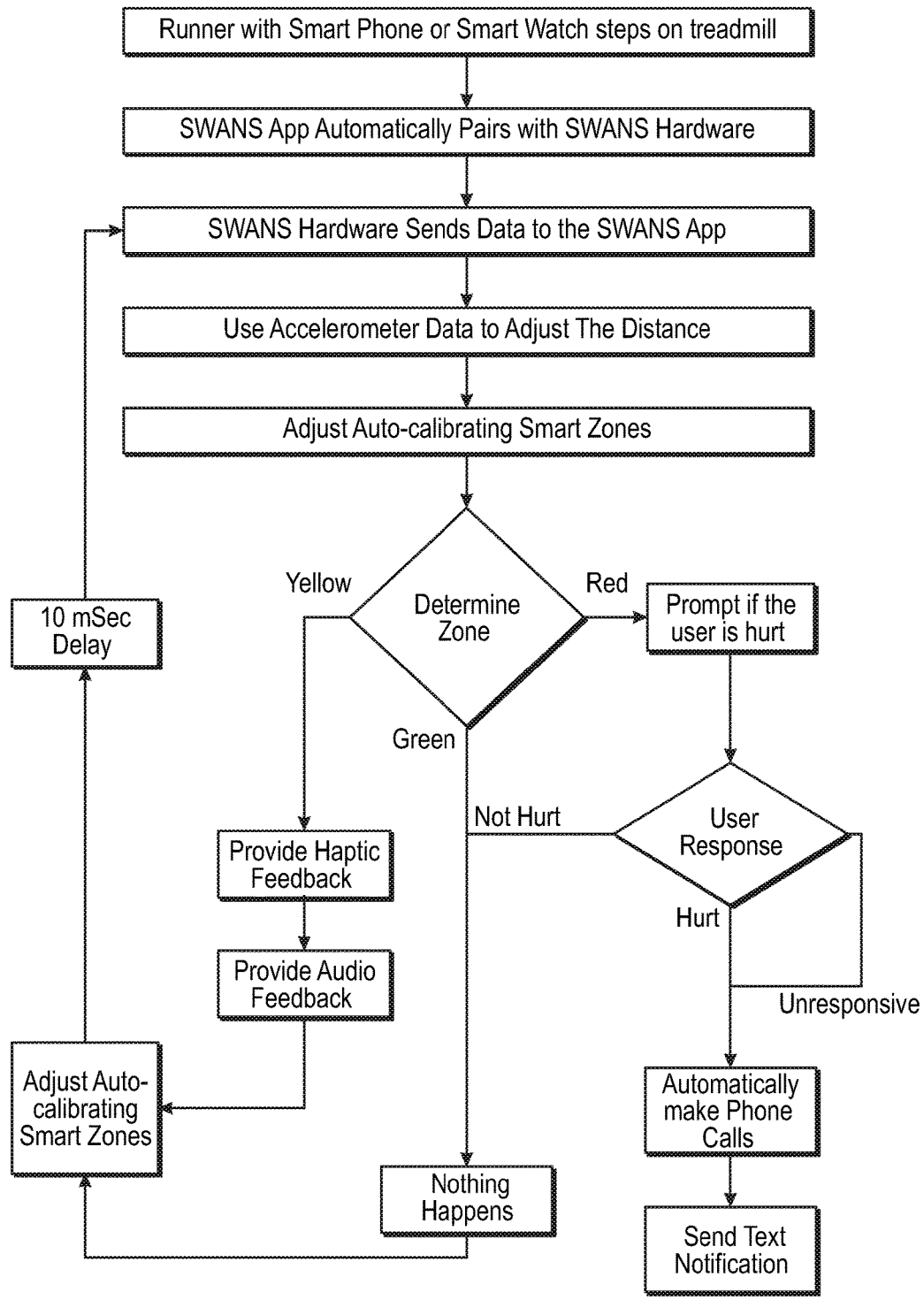
FIG. 13 depicts an exemplary final software decision tree for SWANS.
Figure 15:
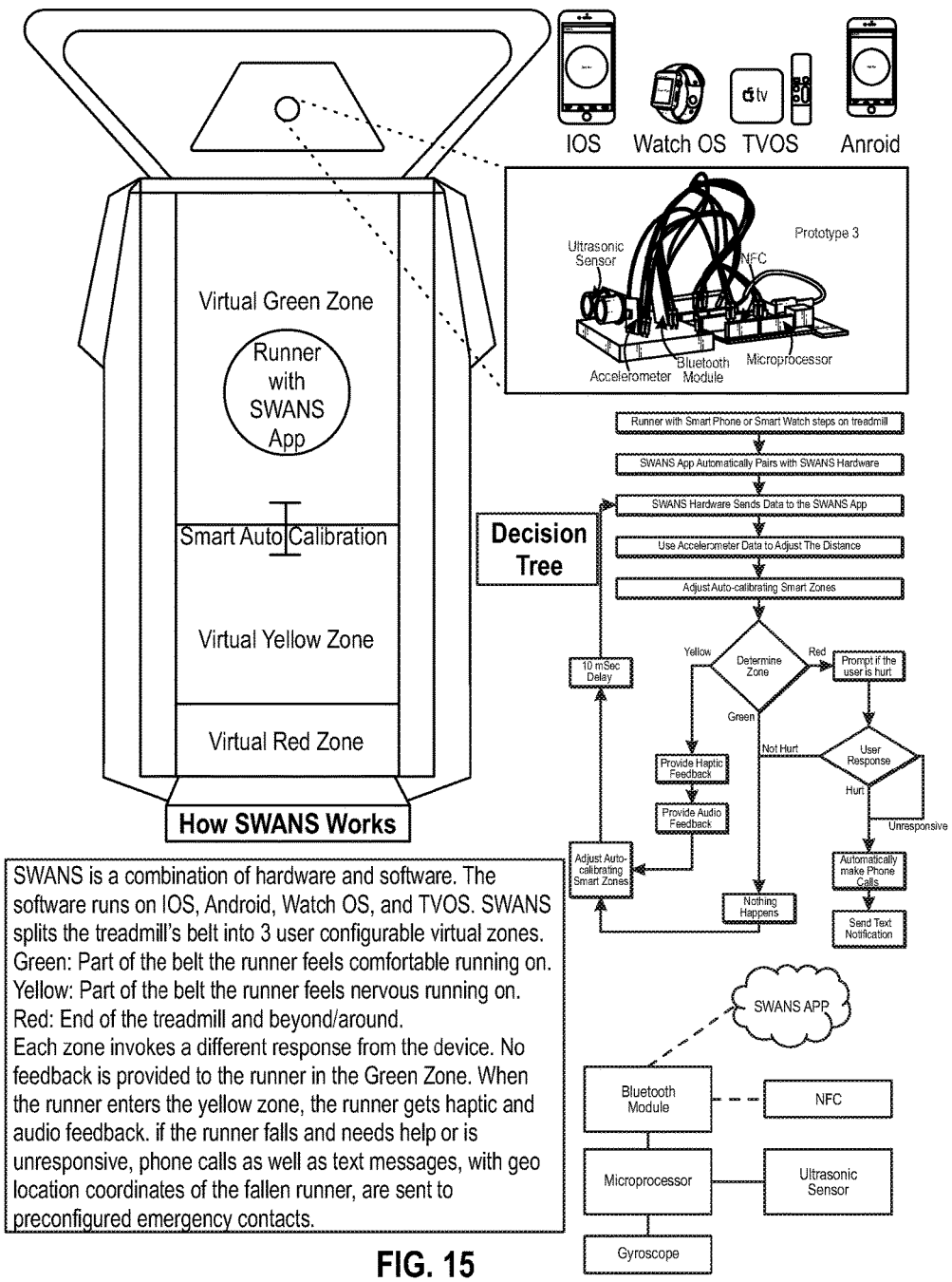
FIG. 15 depicts a schematic diagram of one embodiment of the present invention.

An exemplary additional hardware architecture structure is shown in FIG. 12. An exemplary software decision tree that can be implemented on hardware architecture is shown in FIG. 13. Multiple tests functionality on different devices (smart phones, WatchOS and TVOS) were performed with success results for the exemplary final system described herein, as shown in FIG. 14. An exemplary schematic illustrating one embodiment of the present invention is shown in FIG. 15.

While ultrasonic sensors were discusses herein, infrared sensors or sensors using other technology are contemplated for use according to the present invention as well.

The SWANS system can be a device independent from the treadmill. The user can bring her own, or be provided by the operator and/or the maintenance service (e.g., a gym) such device for using the treadmill. In other embodiments, the SWANS system (or at least the Sensor A part) can be combined to the treadmill (e.g., manufactured as a whole piece or an addible function module).

Other technologies can be combined with SWANS. For example, a video camera can monitor the head or the body position of the user. Whenever such part of body goes beyond a pre-set safety zone (e.g., the head is below a certain height), optionally in combination of SWANS detection of entering the yellow or the red zone, a warning notification can be released by SWANS. Motion detectors can detect the movement of the user, in which a detection of no movement for a certain time can trigger a notification signal too. Safety keys or Harness and Suspension system can also be combined with SWANS, but are not required.

The present disclosure also provides a method of customizing the SWANS system to adapt to personal treadmill usage profiles. Such customization can be done by the treadmill manufacturer, operator, maintainence personnel (e.g., a gym), and/or a user. A customization process can include connecting wearable devices (e.g., a smart phone) to the SWANS system (installed or incorporated in the treadmill or temporarily connected to the treadmill) through, e.g., Bluetooth™ technology, adjusting exercise parameters through the wearable devices (e.g., through a smartphone App) to fit in personalized or customized preference (e.g., the time and difficulty of walking/running on the treadmill, the Green/Yellow/Red zones of the treadmill, the time/ situations for sending out notifications or warnings to the user or another person (e.g., one of her emergency contacts), the emergency contact lists, etc.), and starting exercise on the treadmill.

The present invention further provides a treadmill device incorporated or connected to the SWANS system described herein, wherein a user of the treadmill can personalize or customize the safety issues (e.g., the notification system) through the SWANS.

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the present invention should be determined by reference to the claims, along with their full scope of equivalents, and the specification, along with such variations. Those skilled in the art will recognize, or be able to ascertain using no more than routine experimentation, many equivalents to the specific embodiments of the invention described herein. Such equivalents are intended to be encompassed by the following claims.

I claim:

1. A system for use with a treadmill to detect improper positioning of a user with respect to the treadmill, comprising:
a proximity device removably fixed to the treadmill, said proximity device including a proximity sensor configured to constantly detect a distance between the user and the proximity device when the user is using the treadmill;
a user device wirelessly connected to the proximity device to constantly receive data from the proximity device indicative of the distance between the user and the proximity device, said user device including a processor programmed to:
(a) process the data received from the proximity device to detect whether the user is in an improper position on a belt of the treadmill based on a plurality of zones on the belt of the treadmill, wherein the plurality of zones on the belt of the treadmill includes a first normal operation zone, a second danger zone in which the user is at heightened risk of inadvertently falling off the treadmill, and a third caution zone between the first zone and the second zone, and wherein an alert to the user indicates whether the user is in the second zone or the third zone;

(b) output the alert to the user when the user has been detected to be in an improper position; and (c) automatically issue a notification to a person other than the user to notify the person of a possible emergency involving the user when the user fails to dismiss the alert within a predetermined time period.

2. The system of claim 1, wherein the plurality of zones on the belt of the treadmill is predetermined.

3. The system of claim 1, wherein the plurality of zones on the belt of the treadmill is calibrated by the user using the user device.

4. The system of claim 1, wherein the notification comprises a text message, an email, a phone call, or an alert on a social network.

5. The system of claim 1, wherein the proximity sensor comprises an ultrasonic sensor, an infrared sensor, an optical sensor, a radar sensor, or a capacitive sensor.

6. The system of claim 1, wherein the user device comprises a smartphone, a tablet, a television, or a wearable smart device.

7. The system of claim 1, wherein the user device includes a gyroscope or accelerometer to correct data received from the proximity device due to bouncing movement by the user during use of the treadmill.

8. The system of claim 1, wherein the alert comprises a visual output, an audio output, a haptic output, or an electronic message output.

9. A method of detecting improper positioning of a user on a treadmill, comprising the steps of:

(a) constantly detecting a distance between the user and a proximity device removably affixed to the treadmill when the user is using the treadmill;

(b) wirelessly transmitting data indicative of the distance between the user and the proximity device from the proximity device to a user device;

(c) processing the data received from the proximity device on the user device to detect whether the user is in an improper position on a belt of the treadmill based on a plurality of zones on the belt of the treadmill, wherein the plurality of zones on the belt of the treadmill includes a first normal operation zone, a second danger zone in which the user is at heightened risk of inadvertently falling off the treadmill, and a third caution zone between the first zone and the second zone, and wherein an alert to the user indicates whether the user is in the second zone or the third zone;

(d) outputting the alert to the user when the user has been detected to be in an improper position; and (e) automatically issuing a notification to a person other than the user to notify the person of a possible emergency involving the user when the user fails to dismiss the alert within a predetermined time period.

10. The method of claim 9, wherein the user device includes a gyroscope or accelerometer to correct data received from the proximity device due to bouncing movement by the user during use of the treadmill.

\* \* \* \* \*